United States Patent
Tifft

(10) Patent No.: US 7,035,849 B2
(45) Date of Patent: Apr. 25, 2006

(54) RULES ANALYZER SYSTEM AND METHOD FOR EVALUATING AND RANKING EXACT AND PROBABILISTIC SEARCH RULES IN AN ENTERPRISE DATABASE

(75) Inventor: William Watson Tifft, Tucson, AZ (US)

(73) Assignee: Eclipsys Corporation, Delray Beach, FL (US)

( * ) Notice: Subject to any disclaimer, the term of this patent is extended or adjusted under 35 U.S.C. 154(b) by 192 days.

(21) Appl. No.: 10/349,304

(22) Filed: Jan. 21, 2003

(65) Prior Publication Data

US 2003/0120652 A1 Jun. 26, 2003

Related U.S. Application Data

(62) Division of application No. 09/692,433, filed on Oct. 19, 2000, now Pat. No. 6,829,604.

(60) Provisional application No. 60/160,717, filed on Oct. 19, 1999.

(51) Int. Cl.
G06F 17/30 (2006.01)
(52) U.S. Cl. .................. 707/5; 707/2; 707/4; 707/6
(58) Field of Classification Search .............. 707/3, 707/204, 2, 103 R, 1, 5, 4, 6; 345/700; 705/29
See application file for complete search history.

(56) References Cited

U.S. PATENT DOCUMENTS

| 5,204,939 | A | | 4/1993 | Yamazaki et al. ............. 760/50 |
|---|---|---|---|---|
| 5,832,477 | A | | 11/1998 | Bhargava et al. .............. 707/2 |
| 5,899,991 | A | | 5/1999 | Karch ............................ 707/5 |
| 5,960,430 | A | * | 9/1999 | Haimowitz et al. ............ 707/6 |
| 6,182,070 | B1 | | 1/2001 | Megiddo et al. ................ 707/6 |
| 6,324,534 | B1 | | 11/2001 | Neal et al. ..................... 707/3 |
| 6,618,719 | B1 | * | 9/2003 | Andrei ............................ 707/2 |
| 2002/0002550 | A1 | * | 1/2002 | Berman ......................... 707/3 |
| 2002/0026440 | A1 | * | 2/2002 | Nair .............................. 707/3 |
| 2002/0047858 | A1 | * | 4/2002 | Bayliss et al. ............. 345/700 |
| 2002/0082958 | A1 | * | 6/2002 | Cooley et al. ................ 705/29 |
| 2002/0184248 | A1 | * | 12/2002 | Kachi .......................... 707/204 |

FOREIGN PATENT DOCUMENTS

JP 07271798 A * 10/1995

OTHER PUBLICATIONS

FastEMC 6.2, "UB92 Electronic Claim Submission System", Manual Version: Oct. 31, 1999.*

* cited by examiner

Primary Examiner—Luke S Wasson
Assistant Examiner—Gwen Liang
(74) Attorney, Agent, or Firm—Thomas, Kayden, Horstemeyer & Risley

(57) ABSTRACT

A rules analyzer system and method is provided for an enterprise system to evaluate and rank exact and probabilistic search rules for searching a computer database of records according to the efficiency of each search rule. The rules analyzer collects statistics on the performance of each search rule and assigns a priority value for each search rule according to the collected statistics. The priority values are based on the efficiency or precision of each search rule. Thereafter, the rules analyzer ranks the search rules according to the assigned priority.

13 Claims, 10 Drawing Sheets

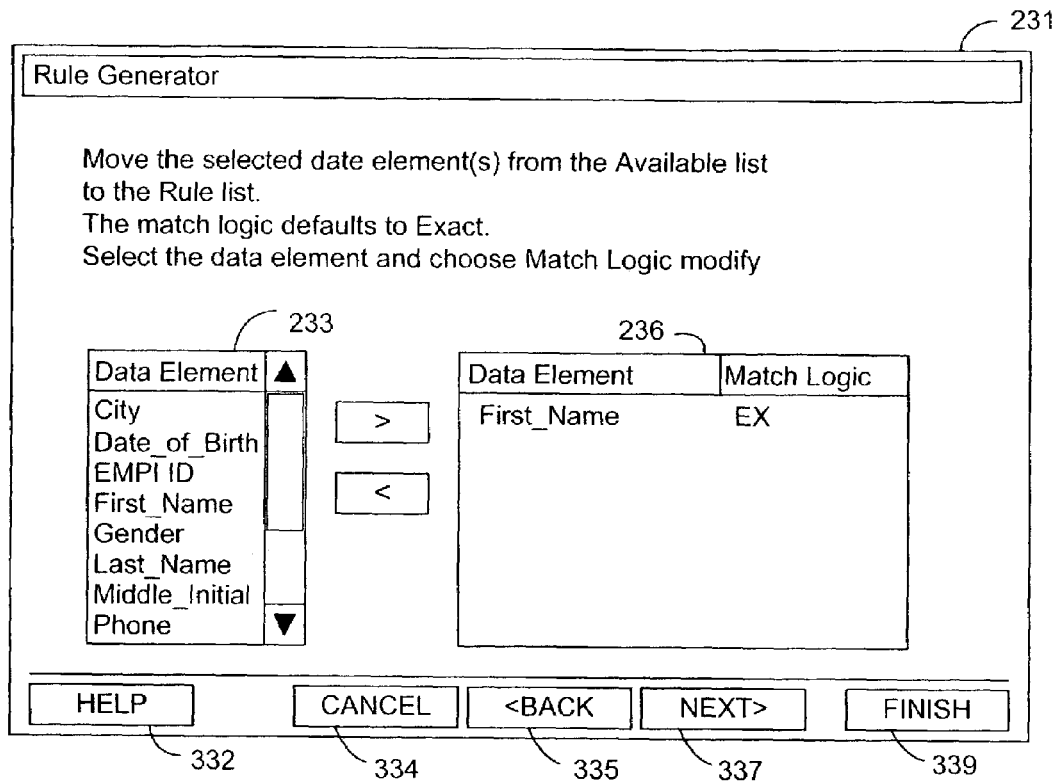
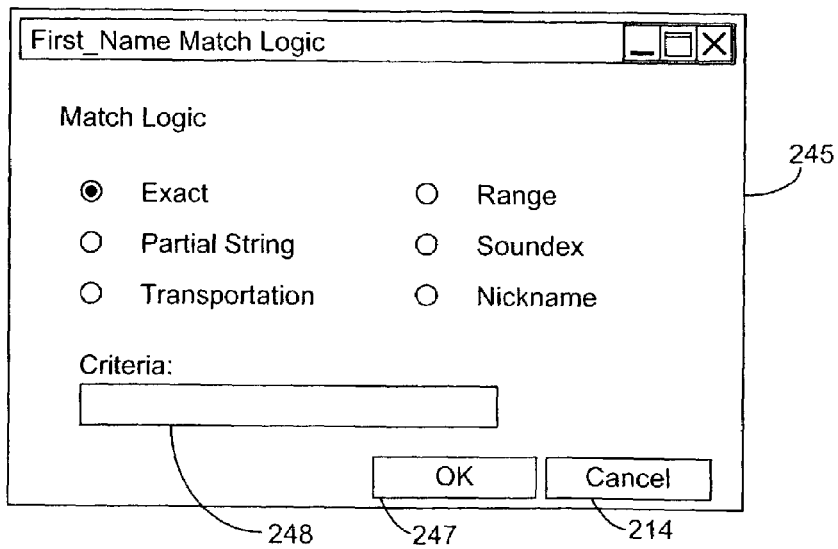
FIG. 5

| Resolve Queue by Rule | | | | | |
|---|---|---|---|---|---|
| Rank | Rule | Rule Type | Description | Total Cases | Unique Cases |
| 1 | 1 | 100% | Enterprise ID Exact | 0 | 0 |
| 2 | 2 | 100% | DOB Exact, First_Name Exact | 0 | 0 |
| 3 | 3 | Likely | Phamis ID Exact | 0 | 0 |
| 4 | 4 | Likely | Last_Name Exact, DOB Exact | 4 | 4 |
| 5 | 5 | Likely | Last_Name Exact, SSN Exact... | 17 | 14 |
| 6 | 6 | Likely | First_Name Partial String (1-2)... | 17 | 14 |
| 7 | 7 | Likely | Last_Name Soundex, First_N... | 3 | 0 |
| 8 | 8 | Likely | Last_Name Exact, DOB Exact | 13 | 9 |

Total Population = 1708
Suspected Duplication Rate = 1.58 %

CLOSE

RULES ANALYZER SYSTEM AND METHOD FOR EVALUATING AND RANKING EXACT AND PROBABILISTIC SEARCH RULES IN AN ENTERPRISE DATABASE

CROSS-REFERENCE TO RELATED APPLICATION

This application is a divisional application of and claims priority to U.S. Utility patent application Ser. No. 09/692,433; filed Oct. 19, 2000, now U.S. Pat. No. 6,829,604, entitled "Rules Analyzer System and Method for Evaluating and Ranking Exact and Probabilistic Search Rules in an Enterprise Database", which claims priority to copending U.S. Provisional Application entitled "Enterprise Person Identifier Method, System, and Computer Program," having Ser. No. 60/160,717, filed Oct. 19, 1999, which is entirely incorporated herein by reference.

BACKGROUND OF THE INVENTION

1. Field of the Invention

This invention relates generally to the data processing field, and more specifically, to a method and system for evaluating the efficiency of and reordering accordingly a plurality of exact and probabilistic enterprise search rules.

2. Description of the Related Art

As healthcare organizations strive to provide maximum value to their customers, access to comprehensive patient information is more important than ever before. The rampant consolidation that has resulted from mergers and acquisitions has made it imperative that providers be able to track a patient across multiple facilities and throughout multiple episodes of care. In many healthcare systems, multiple systems within the same organization are maintained individually resulting in duplicate records of the same person causing confusion if an individual is not entered with exactly the same identification information at each entry point. This task of linking a patient across disparate information systems that are not integrated is a formidable challenge for most organizations; the duplication of critical patient information records caused by manual data entry makes the challenge greater.

For these reasons, an accurate method of identifying individual persons within enterprise is the critical foundation for the healthcare system, so it is essential that master patient identifier systems provide certainty that users are acting upon patient information that is complete, accurate, and updated—that the correct test result is linked to the correct patient. The effects of mistakenly identifying a patient in a healthcare enterprise can be far-reaching, whether the organization comprises one facility or a growing integrated health network. Unnecessary resource utilization, customer dissatisfaction, billing discrepancies and even the possibility of legal exposure from erroneous clinical decisions based on inaccurate patient information—all can be the unfortunate repercussions of maintaining disparate demographic, clinical and financial information about a person that cannot be linked across the enterprise.

Master person index systems are not new, but have never fully addressed the complexities of clearly identifying an individual in today's multi-layered healthcare environment. Some such systems are functionally capable of producing printed reports, others can function with same-vendor systems, and still others rely on hard-programmed matching criteria with limited flexibility. While most master person index systems have been exclusively patient-based or member-based, or have been designed to link systems from a single vendor, effective healthcare delivery in today's environment calls for a more comprehensive solution.

Many master person indexes utilize a series of pre-defined rules to search for the desired target patient records. The rules typically are comprised of a series of elements or fields that enable searching for the desired individual. For example, a rule may include a person's last name, social security number, telephone number, and zip code. Thus, in this example, a user may attempt to find a particular patient by entering the patient's information, and this sample rule would utilize the patient's last name, social security number, telephone number, and zip code. In executing the rule, the system would search the patient database for the same last name, social security number, telephone number, and zip code. The rule would record a hit if it found exact matches for these four data items, but the rule may also record a hit if it found a close match as well. However, if this rule does not find a record that closely matches the data elements for these four data items, no record would be returned and the rule would fail.

Because a given rule may not, and likely will not, always find the desired patient, master person index systems utilize many rules comprised of various data element combinations. In fact, some rules may be implemented in a system that rarely if ever find matches due to the construction of the rule. Therefore, upon firing many different rules, the likelihood of retrieving the correct patient record greatly increases. However, master person index systems create new problems in maintaining many rules and attempting to consider the large number of results that are actually false hits.

The problem with defining rules to locate specific individuals in the enterprise results in situations where some rules are more efficient in finding the correct result that others, but if the good rules are not fired first or before the less-efficient rules, the correct record may be buried in a long list of potential records for the desired individual. Moreover, some rules to locate records may take longer to execute to return the results. Yet other rules may not actually fire if their order is such that the desired number of results is reached by the higher ranking rules. In this situation, the higher ranking rules may not return the correct result while the unfired rule may have. In addition, some rules may have a higher rate of returning duplicate records than other rules, so unless those rules are identified and either adjusted or deleted, their existence reduces system efficiency. Even still, other rules may create a high number of false hits thereby increasing the operator's time in determining the proper record. Finally, rules may be misfired because of data entry errors. Thus, there is a problem in maintaining a set of rules to locate the desired records in an efficient manner.

SUMMARY OF THE INVENTION

A rules analyzer system and method is provided for an enterprise system to evaluate and rank exact and probabilistic search rules for searching a computer database of records according to the efficiency of each search rule. The rules analyzer collects statistics on the performance of each search rule and assigns a priority value for each search rule according to the collected statistics. The priority values are based on the efficiency or precision of each search rule. Thereafter, the rules analyzer ranks the search rules according to the assigned priority.

In another embodiment, system for uniquely identifying an object record in a database of object records according to a plurality of exact and probabilistic search rules is provided.

The system is configured to receive application identification information and attributes that correspond to a target object contained in the database of object records. The system additionally executes one or more exact-match search rules to search the database of object records for the target object. If the exact-match search rules do not return the target record, the system executes one or more user defined probabilistic search rules to search the database of object records for the target object. A list of probable matches to the target object is retrieved by the probabilistic search rules, and the probable matches are ranked by degree of match probability. The user of the system thereafter determines which retrieved record is the target record. Upon selection, the system updates the database of object records in real time for the selected target object with new attributes and information associated with the target object. The system determines the efficiency of the exact-match and probabilistic search rules according to collected statistics for each search rule. Finally the rank order of the exact-match and probabilistic search rules are rearranged in descending order by the efficiency of each search rule.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 5 is a diagram of the rule generator depicted in FIG. 4 for creating a sample rule for execution in the process depicted in FIG. 4.

FIG. 8 is a diagram of a view of search results presented to a user after a search according to the process of FIGS. 6 and 7.

DETAILED DESCRIPTION OF THE INVENTION

Figure 1A:
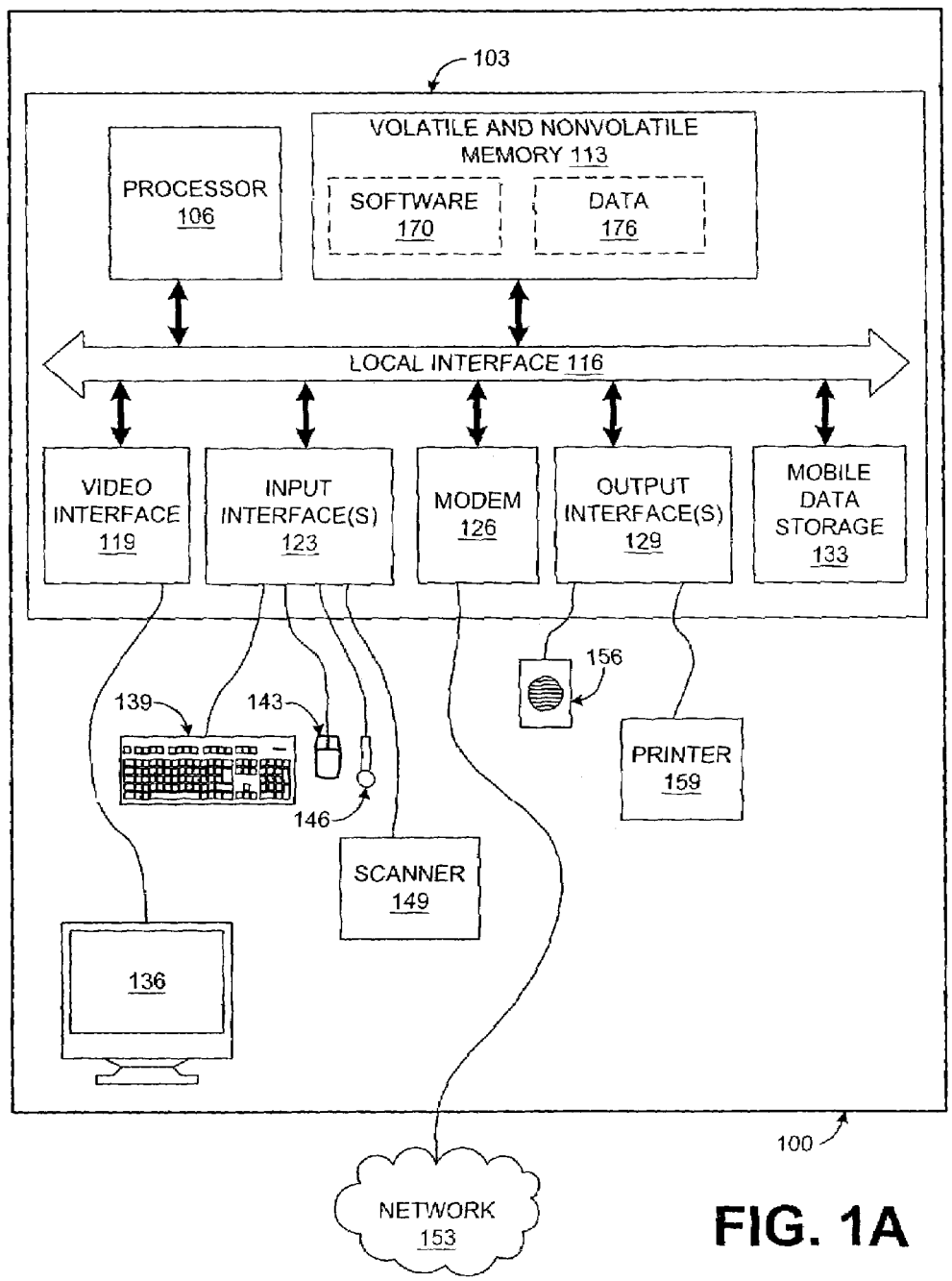
FIG. 1A is a block diagram of a user interface system for implementing the rules analyzer.

Referring to FIG. 1A, shown is a block diagram of a user interface system 100 according to an embodiment of the present invention. The user interface system 100 includes a computer system 103 which comprises a processor 106, and a volatile/nonvolatile memory 113 ("memory 113"), both of which are coupled to a local interface 116. The computer system 103 further comprises a video interface 119, a number of input interfaces 123, a modem 126, a number of output interfaces 129, and a mobile data storage device 133, all of which are also coupled to the local interface 116. The memory 113 may include, for example, a random access memory (RAM), a read only memory (ROM), a hard drive, and other like devices, or any combination of these devices. Note that the term volatile refers to memory devices that generally lose data stored therein upon loss of power, and non-volatile refers to memory devices that do not lose data upon loss of power.

The user interface system 100 also includes a display device 136 which is coupled to the local interface 116 via the video interface 119. The user interface system 100 also includes several input devices, namely, a keyboard 139, a mouse 143, a microphone 146, and a scanner 149 which are all coupled to the local interface 116 via the various input interfaces 123. In addition, the modem 126 is coupled to a network 153 thus allowing the computer system to send and receive data via the network 153. The network 153 may be, for example, the Internet, local area network (LAN), wide area network (WAN), or other similar network.

The user interface system 100 may further include audio speakers 156, a printer 159, or other output devices that are coupled to the local interface 116 via the output interfaces 129. The mobile data storage device 133 may be one of several such devices that allow storage of data on a mobile platform such as a floppy disk drive, compact disc drive, mobile hard drive, mobile fixed memory, or other similar data storage device (none shown in FIG. 1A).

The user interface system 100 also includes document analysis logic 170 that is generally stored on the memory 113 along with data 176. In one embodiment of the present invention, the memory 113 is comprised of a combination of RAM, ROM, and a hard drive, although other combinations may be used. In this embodiment, the document analysis logic 170 is software that is stored on the hard drive and the data 176 is also stored on the hard drive. When the user interface system 100 is operational, pertinent portions of the document analysis logic 170 are loaded into the RAM and is executed by the processor 106. During operation of the user interface system 100, the document analysis logic 170 may access pertinent portions of the data 176 stored on the hard drive, loading them into the RAM for various purposes. For example, the data 176 may comprise a bit map image of a scanned document received from the scanner 149. The data 176 may also be accessed via the mobile data storage 133 or the network 153.

The display device 136 is employed to display any one of a number of interface displays 181 that are viewed by the user. The user interacts with the computer system 103 via the input devices such as the keyboard 139, mouse 143, or microphone 146. The user receives audio output from the audio speakers 156 and the computer system 103 may print out various documents created on the printer 159.

Note that although the above implementation of the present invention is discussed in terms of a processor circuit and software, it is understood that other embodiments of the present invention include a dedicated logical circuit which accomplishes the functionality of the document analysis logic 170, or a combination circuit which includes a processor circuit with software and specific dedicated circuits. It is understood that all such permutations of various implementations are included herein.

Figure 1B:
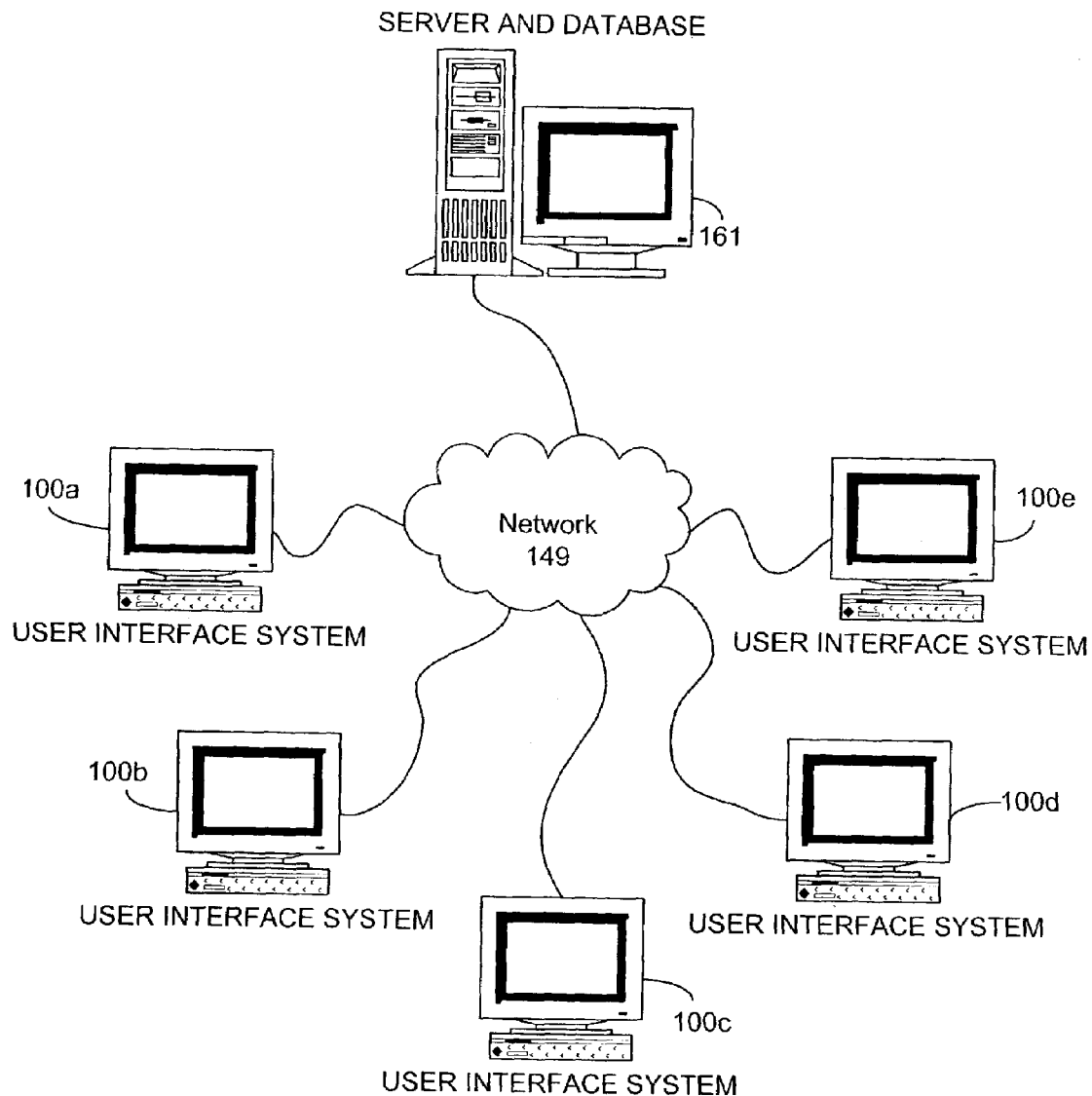
FIG. 1B is a block diagram of multiple user interface systems as depicted in FIG. 1 coupled to a system server and database by a network.

FIG. 1B is a block diagram of multiple user interface systems 100a–100e as depicted in FIG. 1 coupled to a system server and database 161 (also referred to as either system server or system database) by a network 153. Users of any user interface system 100a–100e may send and receive data and other electronic information with system server and database 161. As a non-limiting example, when a user searches for an existing patient on the system server and database 161, the command is initiated at one of the user interface systems 100a–100e. The system server and database 161 receives the command across the network 153 and returns any search results back to the user interface system along the network 153.

One embodiment of the invention includes execution of an enterprise person identifier system (hereinafter "EPI system") source code that executes on the user interface systems 100a–100e and the system server and database 161 to uniquely identify an individual across an enterprise of listings. The EPI system, once configured, enables the determination of whether or not persons (or objects) are potential matches. Based on rules established by a system administrator, the EPI system will either (1) identify persons as a 100% match and update the record for that person in the system server and database 161 with newly entered information, (2) identify persons as possible matches, assign a new identification number, and set aside the likely matches for manual review, or (3) identify the person as unknown to the EPI system, assign a new identification number, and complete the registration process.

For the EPI system to be able to properly locate the correct individual or object, configurable rules are generated to determine whether a person or object that is being presented to the EPI system may already exist in the system server and database 161 (FIG. 1B). The rules are applied when patient lookups, registrations, or updates are initiated from a user interface system 100 (FIG. 1A) or other source system (not shown) that may be capable of communicating with the system server and database 161.

Three main types of rules are typically employed in the EPI system, but it should be obvious to one of ordinary skill in the art that other rule types may also be implemented as well. First, enterprise rules utilize a unique identification number for each individual as part of the rule criteria. Records that have the unique identification number qualify for enterprise rule evaluation or searches. Application rules utilize a source identifier as part of the rule criteria. Records that contain the specified source identifier qualify for an application rule evaluation or search. Finally, generic rules utilize any combination of user-defined data elements, regardless of the source, and do not contain either the unique identification number or the source identifier.

Using rules as described above, each person record comparison has one of the three outcomes. The first possible outcome is an exact or 100% match. Based on user criteria, the system will determine that the newly presented person record is known to the database. This will result in the existing record in the system server and database 161 (FIG. 1B) being updated with the most current data. The second possible outcome is a likely match. Likely matches are matches that are not considered to be 100% or exact matches. Based on user-defined criteria, the system determines that the newly presented person record is suspected to be a duplicate of an existing record in the system server and database 161 and will hold the record for manual review. Finally, the third possible outcome is no match at all. Based on user-defined criteria, the system will determine that the newly presented object record does not match any existing record in the system server and database 161. A new unique identification number is assigned and the person record is established in the system server and database 161 upon recognizing no match.

To maximize the efficiency of the system in quickly and accurately locating person records, the system executes rules in a prescribed order. Irrespective of whether the search is an exact or likely match search, enterprise rules are executed first, application rules second, and generic rules third. If there is more than one enterprise, application, or generic rule defined for the exact or likely rule groups, the order with which the rules engine will evaluate the rules is determined by a ranking order defined for each rule.

Figure 2:
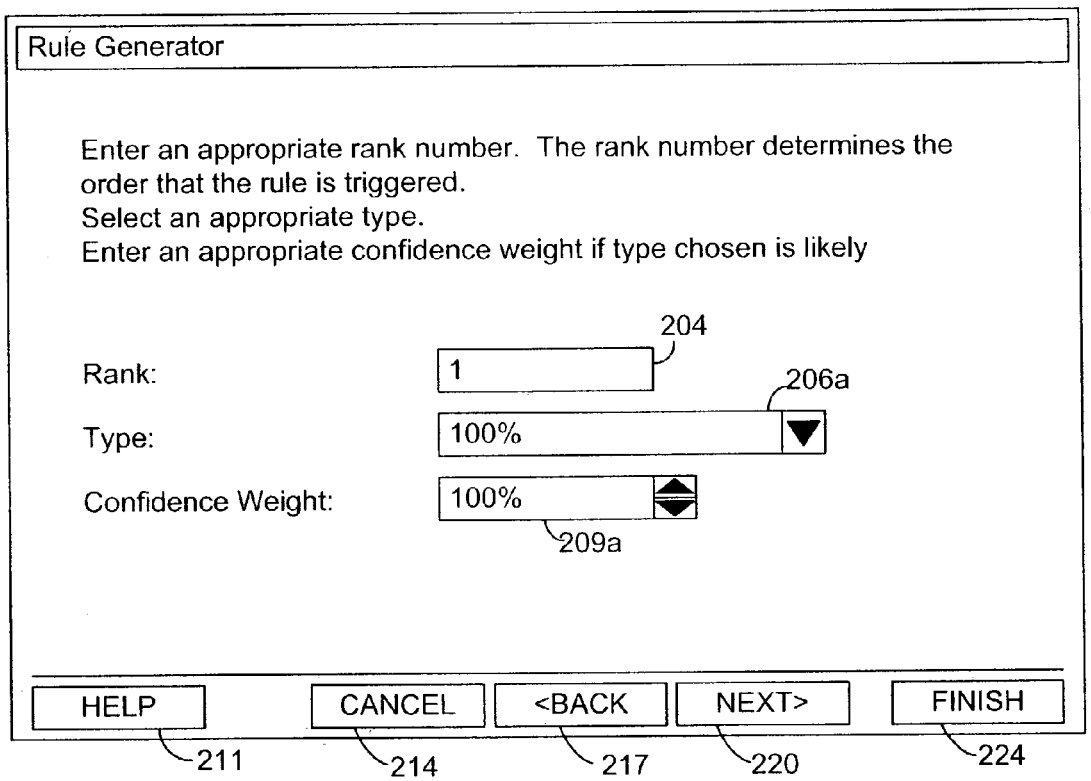
FIG. 2 is a diagram of the rule generator that enables a user to define rules and their rank for execution in the system shown in FIG. 1B.

A system administrator, upon initialization, or periodically, defines the rules used by the EPI system. FIG. 2 is a diagram of the rule generator 201 that enables a user to define rules and their rank for execution in the system shown in FIG. 1B. Upon determination to generate a new rule, the rule generator 201 prompts the system administrator to enter an appropriate rank number for the new rule in block 204. The rank number determines the order that the rule will be triggered within its rule type when a search is commenced. If there is more than one enterprise, application, or generic rule for a rule type, the system will use the rank number 204 to determine which rule should be evaluated first. The type of the rule is entered in block 206a, and in this non-limiting example as depicted in FIG. 2, the type of rule is a 100%, or exact, rule. The two types of rule types for selection include 100% or likely rules. Finally the confidence weight is entered in block 209a, and in this continuing non-limiting example, the confidence weight is 100%. All 100% or exact rules have a confidence weight of 100% because of the nature of that type of rule is either a perfect match or not. Confidence weight values less than 100% are discussed in more detail below. Finally, the rule generator 201 also provides the user-friendly several options, such as help 211, cancel 214, back 217, next 220 and finish 224.

Figure 3:
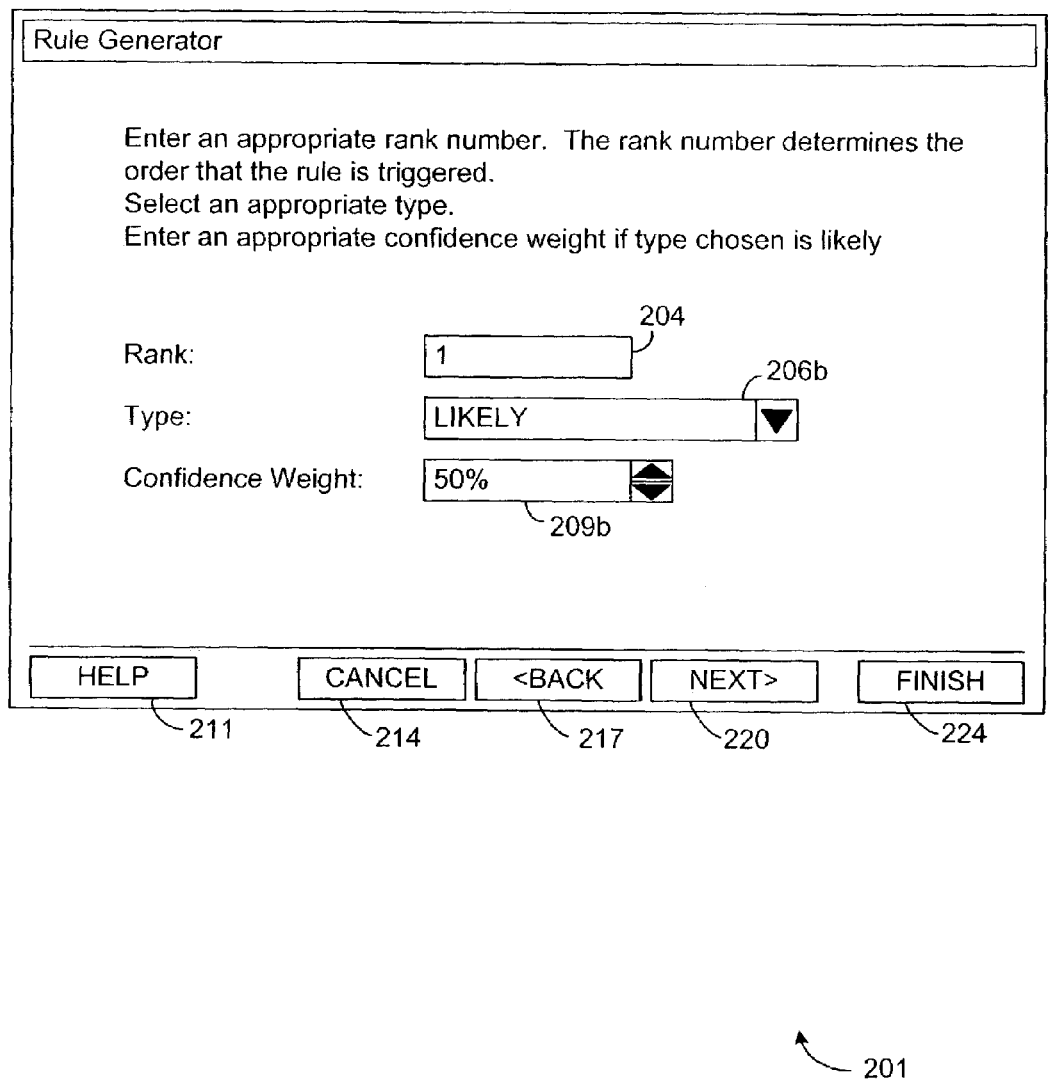
FIG. 3 is a diagram of the rule generator that enables a user to configure the rank of likely rules for execution in the system shown in FIG. 1B.

FIG. 3 is a diagram of the rule generator 201 that enables a user to configure and rank likely rules for the EPI system executed in FIG. 1B. In this non-limiting example, the type of the rule is designated as a likely rule in block 206b. Unlike exact rules, the confidence weight is configured in block 209b as some value between 0 and 99. This number is established by the system administrator in this non-limiting example, but in another embodiment, the rules analyzer itself may also designate the confidence weight based upon the efficiency of the rule.

Figure 4:
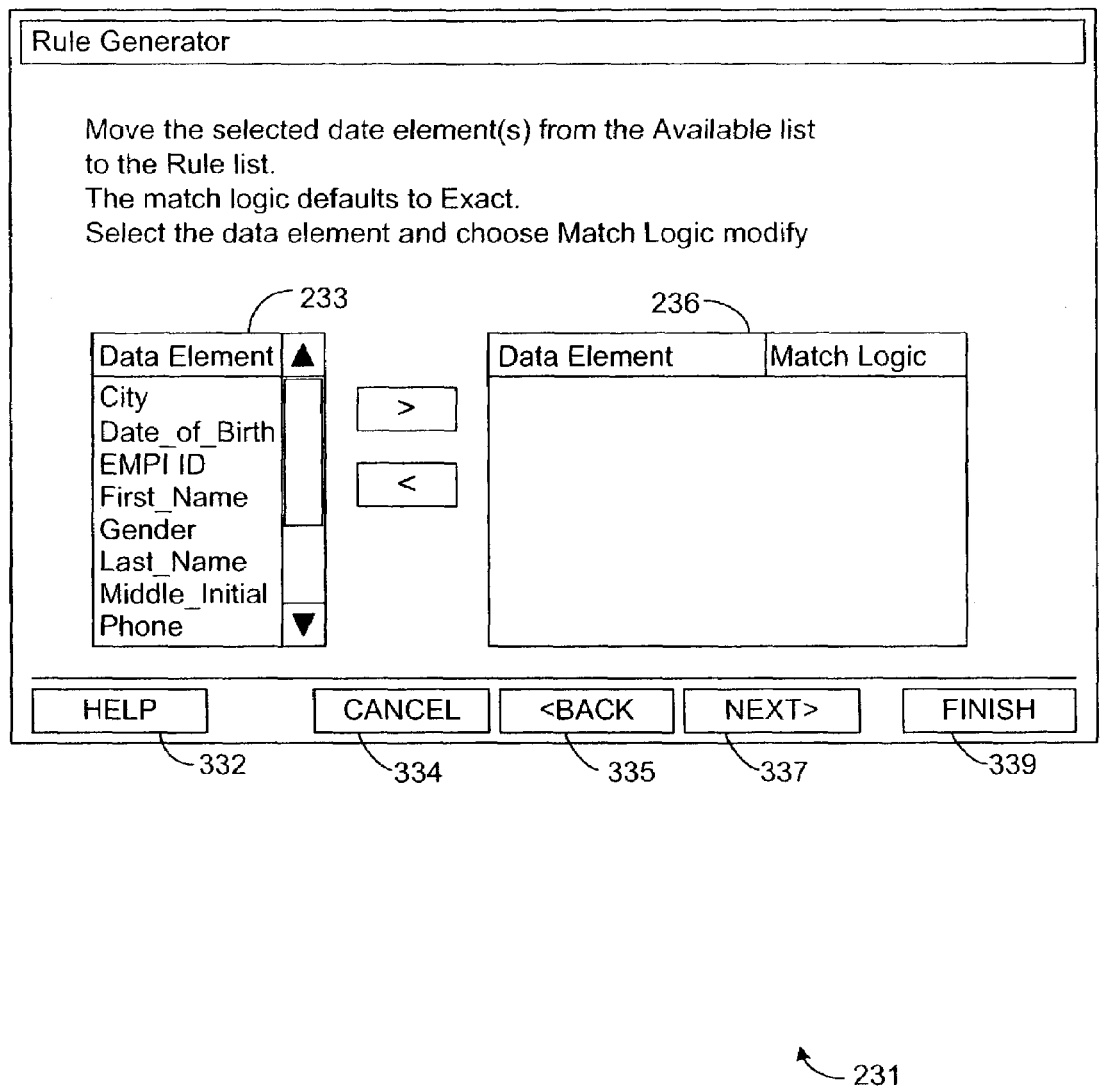
FIG. 4 is a diagram of the rule generator for enabling a user to create the data elements for rules executed in the system shown in FIG. 1B.

After the rank, type, and confidence weight of a rule are established, rule generator 201 prompts the system administrator to select the data elements for the rule. FIG. 4 is a diagram of the rule generator (data element selection) 231 for enabling a user to create the data elements for rules executed in the system shown in FIG. 1B. Data Element field 233 includes a list of various data elements for selection and incorporation into the rule being created. Upon selection, the data element is place in the data element/match logic data field 236. The user may select multiple data elements in data element field 233 for inclusion in the data element/match logic data field 236. As a non-limiting example, the user may elect to include the "First_Name" data element as part of the rule, so that any subsequent search checks the first name of each database object.

FIG. 5 is a diagram of the rule generator 201 depicted in FIG. 4 and a match logic window 245 for selecting the matching logic for each data element placed in the data element/match logic data field 236. Continuing the previous non-limiting example from above, data element "First_Name" is selected in data element field 233 and moved over to data element/match logic data field 236. Upon selecting the "First_Name" data element, the match logic window 245 for "First_Name" enables the system administrator to select between a plurality of choices. In this non-limiting example, the choices include an exact match, partial string match, transportation match, range match, soundex match, and nickname match. The system administrator exits by selecting cancel 214 or may approve of the selection in the match logic window 245 by selecting "OK" 247.

The match logic choices selectable in match logic window 245 enable different types of matches to locate records in a variety of ways. The exact match option, if chosen, provides that the data element string should match the corresponding database object element to qualify for matching. As a nonlimiting example, a search for the last name "Crain" would not return "Crane" as an exact match, but would return last names indicated as "Crain."

Partial string matching logic compares a range of characters entered to the target data in specified character positions entered into data criteria field 248. As a non-limiting example, a system administrator may choose partial string and enter "1–3" for the criteria. Data element values entered will qualify for matching if the first three characters entered match those in the first, second, and third positions of data elements in the system server and database 161. Thus, for a last name partial string search of "Holland" with 1–3 set as the criteria, the results would include "Hollis," "Holt," "Holden," and other names beginning with the letters "Hol."

Transposition matching logic records a match if any two of the string values entered in data criteria field 248 are transposed (switched). Transposition searching actually matches both transposed and exact values. Thus a search for "12345" would return as matches records listed as "12345" and also "12435."

Range matching logic finds matches that fit within a corresponding data criteria field 248. As a non-limiting example, the date of birth may be searched in the range data criteria field 248 by an entry such as "Mar. 24, 1970–Jul. 24, 1970."

Other logic choices that incorporate industry standard devices or plugins may be implemented as well. Soundex is a data element search that employs an industry standard soundex algorithm to identify potential misspellings in the fields of searching.

Finally, the nickname matching logic option searches against a nickname table. For example, A search for "William" may return results with a name of "Bill," and a search for "James" may retrieve records with the name of "Jim."

Figure 6:
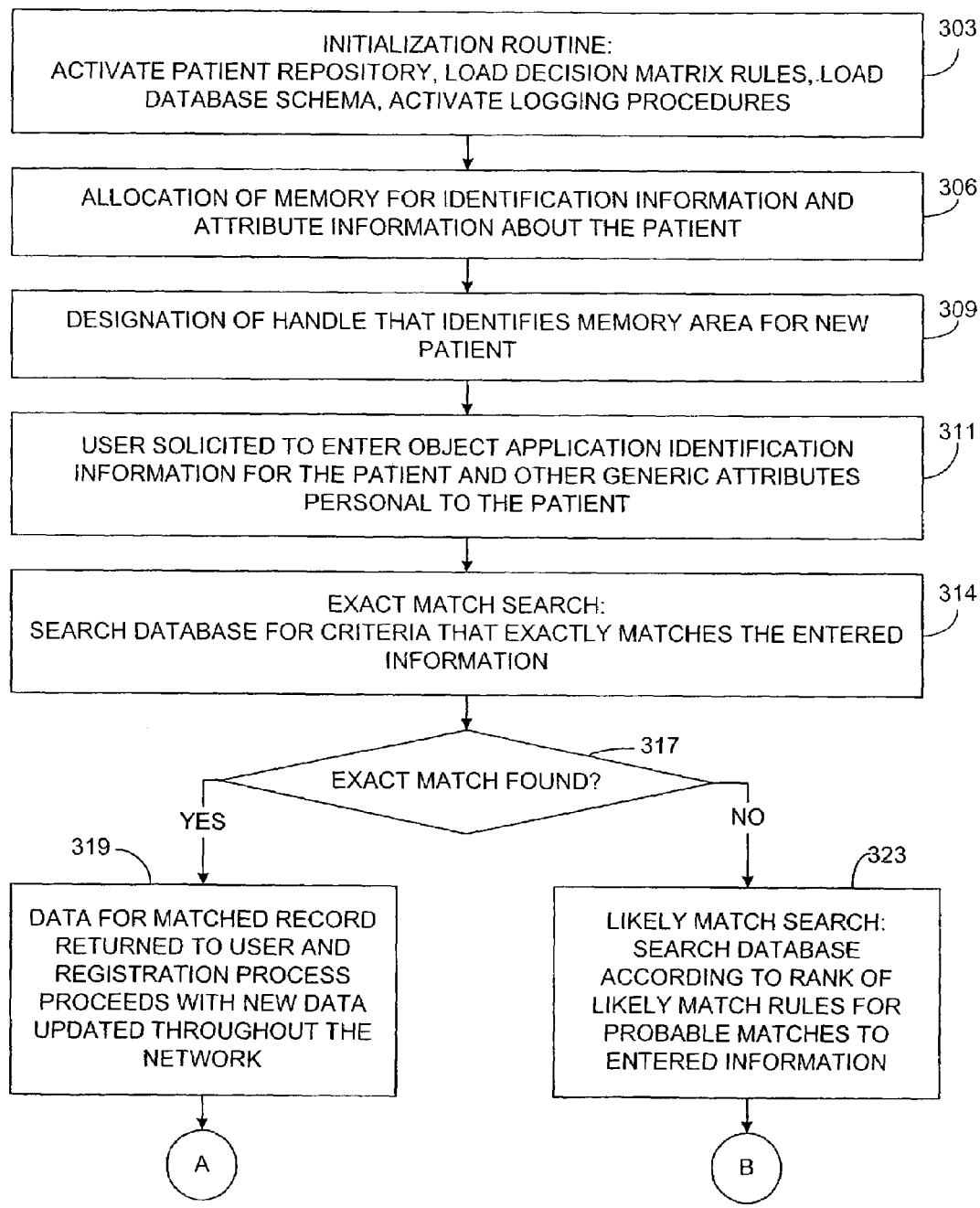
FIGS. 6 and 7 comprise are flowcharts of the process of searching for and finding a particular record according to either exact or likely matching rules, as executed on the user interface system of FIG. 1.
Figure 7:
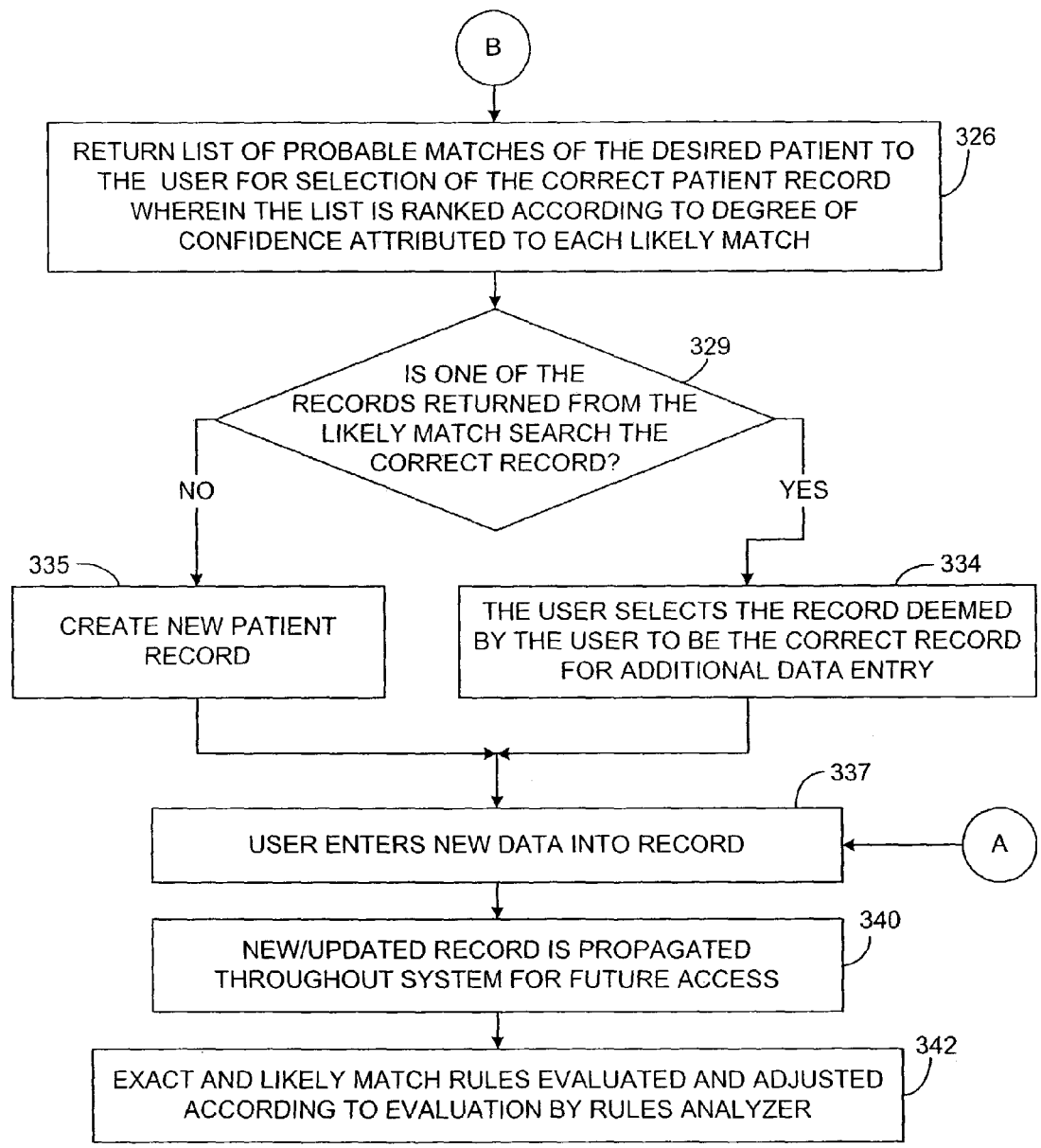

When a user attempts to locate a person's identification information in the system database 161, the EPI system initializes an enterprise person identifier (EPI) search engine to perform a look up. FIGS. 6 and 7 comprise of flowcharts of the process of the software 170 (FIG. 1A) of searching for and finding a particular record according to either exact or likely matching rules, as executed on the user interface system of FIG. 1 and the EPI system of FIG. 2.

Upon initialization, the EPI search engine activates the patient repository, loads the decision matrix rules, loads the database schema, and initializes logging procedures, as in step 303. The patient repository, stored on system database 161 (FIG. 1B), contains the authoritative set of patient records. The decision matrix rules are also loaded from the system database 161 and contain the rules for identifying likely and exact matches. The database schema includes typical data elements such as Last Name, Date of Birth, Social Security Number, etc. Blocks of memory are then allocated in database 161 (FIB. 1B) for storing identification information and attribute information about a new patient, as shown in step 306. A handle is returned designating the area of memory for new patient, as shown in step 309. The EPI system then solicits the user to enter a patient object's application IDs and patient object's generic attributes, as shown in step 311. Entering the application ID and generic attributes of the patient object does not change the system database 161 (FIG. 2) in any way, but merely provides the information to initiate a search.

Based on the information entered by the user, the EPI system performs a search of the system database 161 for an exact match, as shown in step 314. As discussed above, the system administrator defines within the system what constitutes an exact match—such as the number of matched criteria. Also as discussed above, an exact match searches for the identical information as entered by the user on the user interface system 100, as described above in step 311. The EPI system determines whether an exact match is found, as in step 317, and if one is found, the unique single-person identifier created for that entry is returned to the display 136 (FIG. 1) of the user interface system 100 (FIG. 1), as in step 319. In addition, all information in the system database 161 (FIG. 1B) associated with that single patient deemed to be an exact match is also returned, via the network 153, to the user interface system 100. The user then proceeds with the registration process once the person has been correctly linked to the identification number for that patient. When finished, changes to the retrieved record and propagated throughout the enterprise for immediate access by any other user (e.g., access by laboratory personnel for entry of test results).

If no exact match is found in step 317, the EPI system performs a likely match search for the proper patient data record, as in step 323. The likely match routines are based on fuzzy logic routines that search the system database 161 based on the supplied criteria for identification numbers that potentially correspond to the patient object. The EPI system takes the complete list of likely matched identification numbers and scores each retrieved identification number according to the degree of confidence of the match. The identification numbers are sorted into descending order according to the cumulative confidence weight values for each record and presented to the user for selection, as in step 326.

FIG. 8 is a diagram of a view of search results 327 presented to a user after a search according to the process of FIGS. 6 and 7. In this non-limiting example, the search results view depicts both exact and likely search results. The first three rules depicted in FIG. 8 do not show any records as matches, but the fourth rule did return four hits. Rules five through eight also scored at least three records as possible matches to the initial information and attributes (For the purpose of this non-limiting example, the initial information and attributes are irrelevant as the focus depicts how the rules results may be presented to the user.).

Returning to FIG. 7, the user reviews the list of likely matches to determine if any single listing represents the desired patient data record, as in step 329, and if so, then selects that record to enter new information, as depicted in step 334. Once selected, the user updates the selected patient data record with the relevant information, as depicted in step 337. When complete, the update is immediately committed to the system server and database 161 for future reference and entry, as shown in step 340.

If no exact match is found and the list of likely matches does not contain a record listing for the desired patient object, the user can enter any appropriate data for that individual patient and thereby create a new patient record, as shown in step 335. Once entry is complete, this embodiment of the invention immediately and automatically updates the entire enterprise so that any other user will be able to retrieve that patient's data record for future entry.

Periodically, the EPI system activates a rules analyzer to evaluate the efficiency of these previously discussed and enables re-ranking according to their determined efficiency, as shown in step 342. The rules analyzer 342 gathers and records data about rules, rule processing, and the resolution of duplicate patients. By continuously evaluating the rules and their efficiency, the EPI system insures that the rules that most frequently return the correct results are triggered first. The rules that either take too much time to execute or rarely return what is determined to be the correct object record are demoted in rank and eventually deleted by the system operator. The rules analyzer 342 also determines how frequently duplicate records are returned from searches among the set of rules and eliminates rules that are essentially duplicates of other rules. The rules analyzer 342 also, in making sure that the best rules are implemented, identifies rules that do not produce good results thereby increasing the overall efficiency of the EPI system.

Figure 9:
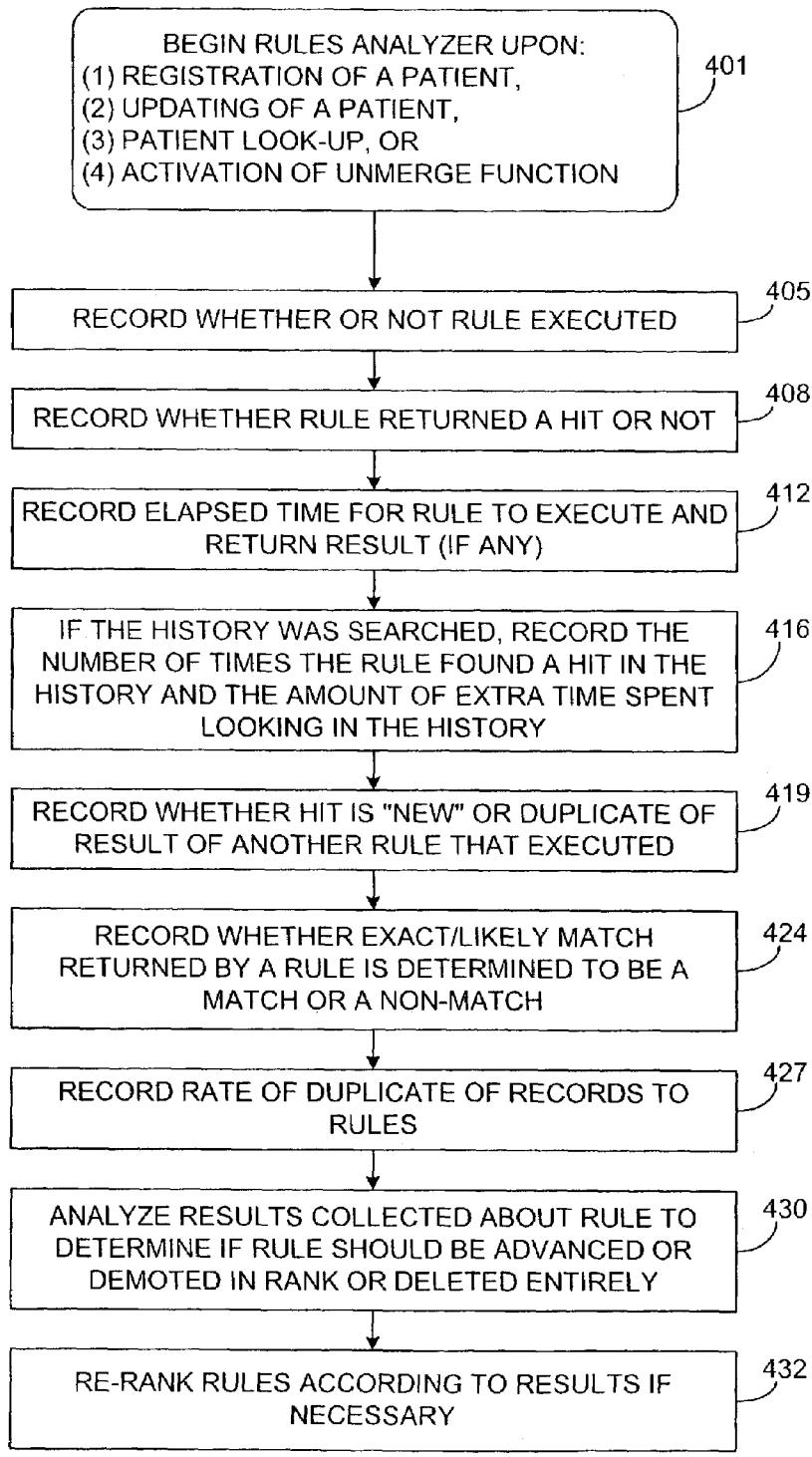
FIG. 9 is a flowchart of the process of the rules analyzer to evaluate the efficiency of rules and to adjust the ranking accordingly executed in the process of FIGS. 6 and 7.

FIG. 9 is a flowchart of the process of the rules analyzer 342 in analyzing the rules and their rankings, as performed in step 342 of FIG. 7. As shown in step 401, the rules analyzer 342 is activated if a patient is initially registered, a record in the EPI system is updated, a search is performed for an individual record, or upon activation of unmerging functions. (Merging occurs when two records are deemed to be the same individual, and unmerging separates previously merged records if needed.)

Once activated, the rules analyzer 342 records whether or not one of the pre-defined rules was triggered or executed, as in step 405. If a rule was fired, the rules analyzer 342 records whether the rule returned a hit from the system database 161, as in step 408. In addition, the elapsed time for the rule to execute and either return a result or not is recorded, as shown in step 412. These variables are recorded in memory 113 (FIG. 1) for subsequent statistical analysis.

The EPI system retains a history of searches and results in memory 113 that may also be searched for a desired object record. If the history is searched, the rules analyzer 342 records the number of instances that the rule returns a result and the amount of additional time taken to search the history, as in step 416.

Since multiple rules may be utilized in a given search, it is possible that two separate rules may return the same record as a hit. Consequently, the rules analyzer 342 records whether each returned result is a new hit or a duplicate hit from another rule execution, as in step 419.

As discussed above, the EPI system causes the user interface system 100 to present the user the list of likely matches for selection of the correct object record. If one of the returned records is determined to be the correct record from the list of returned results, the rules analyzer 342 records which rule found the record that was determined to be the correct rule, as in step 424.

The rules analyzer 342 additionally records the overall duplication rate of the entire EPI system (i.e., when a new person is registered in the system, what percentage of the time is a match found and what is the number of matches found?). One aspect of the EPI system is that it operates to eliminate duplicate records, so the rules analyzer 342 maintains statistics on the efficiency of reducing duplicate records.

The information recorded as discussed above is place in a database table contained in the system server and database 161 (FIG. 1B). The rules analyzer 342 places the information in either a RuleFiring table or a MatchResolution table (neither are shown except as contained in database 161). From there, either a user can review the results and alter the rule rankings or the rules analyzer 342 itself may be configured to do so.

The RuleFiring table contains the following columns of data for implementation by the rules analyzer 342:

| Column Name | Description of Column |
|---|---|
| RuleFiringID | Unique DB identifier |
| RuleName | Rule name known to user |
| EventType | Type of even triggering the execution of a rule |
| EventWhen | Date and time event occurred |
| RuleGrpName | Rule group that was active when trigger occurred |
| ClientType | Type of client: HL7 interface, batch extractor, or EPI client |
| ComputerName | name of client computer initiating trigger event |
| RulePriority | Priority/order of firing within rule group |
| FiredWhen | Date/time rule fired |
| MatchesFound | Total Matches found by the firing (0 or 1 for Exact Rules; 0, 1, or more for Likely Rules) |
| NewMatchesFound | Matches found by this firing that are not duplicates |
| MissingDataFirings | Requests to fire a rule that are skipped due to missing data |
| HistoryMatchesFound | Number of matches found in the history table |
| TotalSearchTime | Time the rule spent searching the database for matches recorded in 100ths of second |
| SourceName | Source of the triggering event |
| InitiatingUser | User who initiated the trigger event |
| ResolvingUser | User who did the resolution |
| HistorySearchTime | Time the rule spent searching the history |
| SoundexSearchTime | Time the rule spent searching soundex |

The MatchesFound column above includes data regarding the total number of potential matches found by a rule firing. For an exact rule, it is either zero or one. For a likely rule, it may be zero, one, or more. NewMatchesFound applies to likely rules and not to exact rules, and it records the number of matches found that are not already in the likely table (i.e., they are new rather than duplicates). Thus, MatchesFound=NewMatchesFound plus duplicates found. For an exact rule, NewMatchesFound equals MatchesFound (0 or 1).

Rules can include a variety of data elements in the rule definition—last name and social security number are examples of data elements. If a user fails to enter all the data elements required by a rule, the rule cannot be fired. As a non-limiting example, if a user enters registration data about a patient but omits social security number, then rules containing social security number cannot be fired. Likewise if an input file containing patient data omits social security number then rules containing social security number cannot be fired when the file is processed. Since every rule is a tool for eliminating duplicate records, careless data entry reduces the benefits of the system by preventing impacted rules from performing their function.

The rule analyzer 342 addresses this problem by recording both standard firings (when a rule fires normally) and "missing data firings" (requests to fire a rule that are skipped due to missing data). The RuleFiring table contains rows representing both kinds of rule firing, so that total firings=standard firings+missing data firings. The RuleFiring table also contains information about the computer and the user who initiated the event that led to the rule firing request. The user can inspect this data to determine which rules are being impacted by missing data and who is failing to enter the data. The results of the RulesFiring table enable users to be reeducated regarding data entry process so that all the rules are fired as planned.

The MatchResolution table contains the following columns of data for implementation by the rules analyzer 342:

| Column Name | Column Description |
| --- | --- |
| MatchResolnID | Unique DB Identifier |
| RuleFiringID | DB identifier of RuleFiring row that generated the likely match |
| ComputerName | Name of client computer initiating resolution |
| ResolvingUser | User who did the resolution |
| ResolvedWhen | When likely math was resolved |
| ResolutionType | Resolved as a match or non-match |

Returning to FIG. 9, once the rules have fired and the records discussed above have been collected, the results are analyzed for determination of whether the rule ranking needs adjustment, as in step 430. In one embodiment, the evaluation and adjustment, as in step 342, may be manual by the system administrator.

In this embodiment, the EPI system compiles data from the tables above into summary tables, RuleFiring_Smry and MatchResoln_Smry (not shown) for reporting purposes. The RuleFiring_Smry contains data that summarizes the RuleFiring table and the MatchResoln_Smry table contains data that summarizes the MatchResolution table. One row in each summary table contains data that summarizes many rows in its corresponding data table. The summary tables are populated by a post-processing routine that reads rows form the data tables and writes corresponding summary rows to the summary tables. The rule analyzer 342 reports are produced from the summary tables not from the data tables. From these reports, a user may reorder the rank or priority of each rule.

As stated above, the EPI system enables a user to set the rank or priority of each rule so that rules are executed according to a pre-set order, which desirably is according to the probability that a rule will find a match. Since the exact rules are fired first and the likely rules fired afterwards, the two rule types are treated separately—exact rules as a group have first priority followed by likely rules. A rule efficiency report depicts probability values for each exact rule and a rule precision report depicts probability for each likely rules.

The efficiency of a rule is calculated as the percentage of rule firings in which the rule finds a possible match. For an exact rule, possible matches are real matches by definition, so for exact rules, efficiency is the same as the probability of finding a match. As a non-limiting example, if an exact rule fires ten times and on four occasions finds a hit and on six occasions finds nothing, then the efficiency equals the probability of finding a match, or 40%. The rule efficiency report reports the efficiency of all the rules. The administrator can use the efficiencies of the exact rules to assign their priorities using the EPI system.

The precision of a rule is the percentage of possible matches found by a rule that are manually determined to be real matches. Precision computations apply to likely rules. As a non-limiting example, if a likely rule has produced 100 possible matches and 60 of these have been manually resolved and 40 are still waiting to be resolved. Suppose that of the 60 that have been resolved, 20 are determined to be matches and 40 are deemed to be non-matches. The precision value for this rule would be (20/60)*100=33%. The system administrator can use the precision report to assign priority values to likely rules in the EPI system. This number could also be used to set the confidence weight as described above.

In another embodiment, the rules analyzer 342 may itself implement an evaluation algorithm to consider the variables discussed above to generate an index number equating to an efficiency value for each rule. The mechanism for automatic adjustment is implemented similarly as for the manual case previously described. As described above, the rules analyzer 342 determines the efficiency of each exact rule and the precision of each likely rule. Periodically, a the rules analyzer 342 spawns an algorithm that adjusts the rank of the rules according to the efficiency and precision data for each rule, as in step 432.

Any process descriptions or blocks in flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

The EPI system, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner, and then stored in a computer memory. It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The invention claimed is:

1. A method of uniquely identifying an object record in a computer database of object records according to a plurality of ranked exact and probabilistic search rules, comprising the steps of:
   obtaining application identification information and attributes of a target object;
   executing one or more exact-match search rules to search the database of object records for the target object;
   executing one or more user defined probabilistic search rules to search the database of object records for the target object if the exact-match search rules retrieve no object record identical to the obtained application identification information and attributes, wherein a list of probable matches to the target object are retrieved and ranked by degree of match probability;
   receiving user input of selection of one retrieved object record determined to be the target object record;
   updating the database of object records in real time for the selected target object with new attributes and information associated with the target object;
   determining an efficiency measure for each of the exact-match and probabilistic search rules according to a plurality of collected statistics for each search rule; where the efficiency measure measures how efficient a corresponding search rule is in finding a match with the target record; and
   adjusting a sequence of execution of the exact-match and probabilistic search rules in descending order by efficiency measure,
   wherein one of the collected statistcs corresponds to a number of instances that one of the probabilistic search rules retrieves one or more possible matches to the target object record, or to a number of instances that one of the probabilistic search rules retrieves a record previously retrieved by a previously executed search rule, or to a number of instances that one of the probabilistic search rules retieves a record that was not retrieved by a previously executed search rule, or to a number of instances that one of the probabilistic search rules retrieves a plurality of records subsequently determined to correspond to the target object record, or to a number of retrieved records that are determined not to be the target object record.

2. The method of claim 1, further comprising the step of:
   creating a new object record if the exact-match or probabilistic search rules fail to return a record determined by the user to be the target object.

3. The method of claim 1, wherein the exact-match search rules are executed according to a pre-configured rank order.

4. The method of claim 1, wherein the probabilistic search rules are executed according to a pre-configured rank order.

5. A computer system tangibly embodied in a computer readable medium for uniquely identifying an object record in a computer database of object records according to a plurality of exact and probabilistic search rules, comprising:
   instructions to obtain application identification information and attributes corresponding to a target object contained in the database of object records;
   instructions to execute one or more exact-match search rules to search the database of object records for the target object;
   instructions to execute one or more user defined probabilistic search rules to search the database of object records for the target object if the exact-match search rules retrieve no object record identical to the obtained application identification information and attributes, wherein a list of probable matches to the target object are retrieved and ranked by degree of match probability;
   instructions to receive user input of selection of one retrieved object record determined to be the target object record;
   instructions to update the database of object records in real time for the selected target object with new attributes and information associated with the target object;
   instructions to determine the efficiency of the exact-match and probabilistic search rules according to a plurality of collected statistics for each search rule; and
   instructions to adjust a sequence of execution of the exact-match and probabilistic search rules in descending order by the efficiency,
   wherein one of the collected statistics corresponds to a number of instances that one of the probabilistic search rules retrieves one or more records as possible matches to the tares object record, or to a number of instances that one of the probabilistic search rules retrieves a record previously retrieved by a previously executed search rule, or to a number of instances that one of the probabilistic search rules retrieves a record that was not retrieved by a previously executed search rule, or to a number of instances that one of the probabilistic search rules retrieves a plurality of records wherein the plurality of records are subsequently determined to correspond to the target object record, or to a number of records that are determined not to be the target object record.

6. The system of claim 5, further comprising the step of:
   instructions to create a new object record if the exact-match or probabilistic search rules fail to return a record determined by the user to be the target object.

7. The system of claim 5, wherein the exact-match search rules are executed according to a pre-configured rank order.

8. The system of claim 5, wherein the probabilistic search rules are executed according to a pre-configured rank order.

9. A rules analyzer method to evaluate and rank search rules for searching a computer database of records, comprising the computer-implemented steps of:
   collecting a first plurality of statistical performance values regarding execution of at least one exact-match search rule, wherein said execution searches for a target object record;
   collecting a second plurality of statistical performance values regarding execution of each at least one probabilistic search rule;

assigning a priority value for each of the exact-match and probabilistic search rules according to the collected statistical performance values; and ranking the exact-match and probabilistic search rules in descending order according to the assigned priority values, wherein one of the second plurality of statistical performance values corresponds to a number of instances where execution of one of the probabilistic search rules retrieves one or more possible matches to the target object record, or to a number of instances where execution of one of the probabilistic search rules retrieves a record previously retrieved by a previously executed search rule, or to a number of instances where execution of one of the probabilistic search rules retrieves a record not retrieved by a previously executed search rule, or to a number of instances where execution of one of the probabilistic search rules retrieves a plurality of records subsequently determined to correspond to the target object record, or to a number of retrieved records that are determined not to be the target object record.

10. The method of claim 9, further comprising the computer-implemented step of:

determining an efficiency of each exact match search rule according to the collected statistical performance values, wherein the efficiency is a percentage of instances that an exact match search rule returns a possible match upon execution.

11. The method of claim 9, further comprising the computer-implemented step of: determining a precision of each probabilistic match search rule according to the collected statistical performance values, wherein an efficiency is a percentage of possible matches retrieved by the probabilistic match search rule that are resolved as real matches.

12. A rules analyzer system tangibly embodied in a computer readable medium to evaluate and rank search rules for searching a computer database of records, comprising:

means for collecting a first plurality of statistical performance values regarding execution of at least one exact-match search rule, wherein said execution searches for a target object record;

means for collecting a second plurality of statistical performance values regarding execution of each at least one probabilistic search rule;

means for assigning a priority value for each of the exact-match and probabilistic search rules according to the collected statistical performance values; and means for ranking the exact-match and probabilistic search rules in descending order according to the assigned priority value, wherein one of the second plurality of statistical performance values corresponds to a number of instances where execution of one of the probabilistic search rules retrieves one or more possible matches to the target object record, or to a number of instances where execution of one of the probabilistic search rules retrieves a record previously retrieved by a previously executed search rule, or to a number of instances where execution of one of the probabilistic search rules retrieves a record not retrieved by a previously executed search rule, or to a number of instances where execution of one of the probabilistic search rules retrieves a plurality of records subsequently determined to correspond to the target object record, or to a number of records that are determined not to be the target object record.

13. The system of claim 12, further comprising:

means for determining an efficiency measure of the exact-match search rule according to the collected statistical performance values, wherein the efficiency measure is a percentage of instances that an exact match search rule returns a possible match upon execution; and means for determining a precision of the probabilistic match search rule according to the collected statistical performance values, wherein an efficiency is a percentage of possible matches retrieved by the probabilistic match search rule that are resolved as real matches.

* * * * *